United States Patent [19]

Van Deursen et al.

[11] Patent Number: 5,245,108
[45] Date of Patent: Sep. 14, 1993

[54] CYCLOOLEFIN PURIFICATION METHOD

[75] Inventors: Josephus H. Van Deursen; Petrus A. J. M. Hendriks, both of Amsterdam, Netherlands

[73] Assignee: Shell Research Limited, United Kingdom

[21] Appl. No.: 924,965

[22] Filed: Aug. 5, 1992

[30] Foreign Application Priority Data

Aug. 29, 1991 [EP] European Pat. Off. ......... 91202203.5

[51] Int. Cl.$^5$ .............................................. C07C 7/12
[52] U.S. Cl. ..................................... 585/831; 585/820
[58] Field of Search ................................ 585/831, 820

[56] References Cited

U.S. PATENT DOCUMENTS 4,584,425 4/1986 Tom .................................... 585/827

FOREIGN PATENT DOCUMENTS 0084888 8/1983 European Pat. Off. .
0217130 1/1990 Japan .

Primary Examiner—Anthony McFarlane
Assistant Examiner—Nhat D. Phan

[57] ABSTRACT

A process for selectively reducing the 5-isopropenyl-2-norbornene content of a dicyclopentadiene composition by contacting a 5-isopropenyl-2-norbornene containing DCPD composition with an acid clay.

6 Claims, No Drawings

CYCLOOLEFIN PURIFICATION METHOD

The present invention relates to a method for reducing the impurity content of cycloolefins and more in particular of dicyclopentadiene (DCPD). to the purified DCPD thus prepared and to its use.

DCPD is a versatile chemical which is known to be used as starting material for the preparation of numerous compounds, such as for example compounds which find use as agrochemical or as pharmaceutical A further outlet for DCPD is as monomer for the preparation of polymeric materials, such as DCPD homo- and copolymers. An important class of DCPD based polymers are the ethylene/propylene/cyclic diene copolymers, known as EPDM rubbers. A special class of DCPD based thermoset polymeric materials are those prepared via a polymerization process which is conducted in the presence of a ring-opening, metathesis catalyst system. Such a process has been described e.g. in European Patent Specification EP 0 084 888.

The performance properties of the thermoset polymeric materials prepared according to said process are closely related to the purity of the DCPD used. For some applications a DCPD feedstock having a DCPD content of only 97% is sufficient or even advantageous, while for other applications at least 99% pure DCPD is required.

The purity of DCPD is however not only important for the type of application and/or for the level of performance properties of the ultimate polymeric material, but may also affect the polymerization reaction time, as it is known that some of the compounds which may be present in DCPD can act as catalyst poison, while others tend to delay the onset of the polymerization reaction. Hence the purification and/or upgrading of DCPD has attracted a lot of attention.

In U.S. Pat. No. 4,584,425 a number of methods for reducing the impurity content of DCPD have been discussed. Next to drying of DCPD these include the removal of volatile impurities via distillation as well as contacting the DCPD to be purified with one or more adsorbents. In this context it is stated that a Linde 10 A molecular sieve (Union Carbide Type 13 X M.S.) is one of the most effective adsorbents. Moreover, it is also stated that the 13 X mol sieve is more effective than alumina in reducing the delay time of DCPD.

It was mentioned in Japanese Published Patent Application JP 02 17130 that a method for lowering the freezing point of DCPD. which comprises mixing for example 5.alkylidenebicyclo[2.2.1]hepto-2-ene or 5-alkenylbicyclo[2.2.1]hepto-2-ene with DCPD, had the disadvantage that both said additives inhibit the synthetic resin forming reaction and moreover adversely affect the properties of the synthetic resin obtained.

The 13 X mol sieve treatment of crude DCPD, as described in U.S. Pat. No. 4.854.425 was further studied by the present inventors, and it was observed that said 13 X mol sieve treatment did not only result in a reduction of the delay time but moreover in a general reduction of the alkenylnorbornenes content of DCPD. By further experimentation it was found that there appears to be some correlation between the delay time of DCPD and its alkenylnorbornene content, which phenomenon more or less supports the statement in the aforesaid Japanese Patent Application, on the harmful effect of the presence of 5-alkenylbicyclo[2.2.1]hepto-2-ene in DCPD. However, it was simultaneously found that the DCPD that had been treated with 13 X mol sieve, still contained appreciable quantities of the 5-isopropenyl-2-norbornene.

The presence of alkenylnorbornenes in DCPD results from the feedstock used for the production of DCPD. DCPD is generally produced by dimerization of cyclopentadiene (CPD), which is one of the components of the $C_5$-effluent stream from a naphtha cracker, which stream generally also comprises non-cyclic dienes such as isoprene and piperylene. When said $C_5$-stream is cooled to a temperature in the range of e.g. 100° C. or lower, dimerization of CPD will generally occur. Although most of the CPD will be converted to the corresponding dimer, i.e. DCPD, occasionally very small quantities of CPD oligomers may also be formed, which compounds were however not expected to hamper the polymerization reaction. Other compounds which may be formed during the dimerization include the aforesaid alkenylnorbornenes, being the reaction product of CPD and the noncyclic dienes, and which will hereinafter be referred to as codimers. Generally the dimerized $C_5$-stream is subjected to flashing or distillation in order to separate a substantial part of the lower boiling components, e.g. the non-converted $C_5$-fractions, leaving a residue substantially comprising mixtures of DCPD and codimers. The codimer content of such a DCPD composition may be reduced by submitting it to a thermal treatment at a temperature in the range of from e.g. 150°-170° C. as a result of which the dimer compounds are converted to the corresponding monomeric compounds. Upon cooling, dimerization will occur and provide a DCPD composition being richer in DCPD than the previous one, as well as containing some non-cyclic conjugated dienes, which compounds can again be removed via flashing or distillation. When desirable, the thermal treatment/dimerization procedure can be repeated until a DCPD composition has been obtained, having the required degree of purity It will be appreciated that such purification steps will have a significant impact on the price of DCPD.

Another disadvantage of the aforesaid DCPD decomposition/recombination procedure for reducing the codimer content of DCPD, is the fact that it is not selective, i.e. in addition to the conversion of the codimer to CPD and a non-cyclic diene, the DCPD is also decomposed. Moreover the relatively high temperatures employed could risk the formation of other contaminants.

Hence it can be concluded that there is considerable need for a simple and improved method for reducing the codimer content of DCPD.

The problem underlying the present invention is developing a method for reducing the codimer content of DCPD which does not suffer from one or more of the disadvantages as described hereinbefore.

As a result of extensive research and experimentation it was surprisingly found that the codimer content of DCPD, and in particular the 5-isopropenyl-2-norbornene content, could efficiently be reduced by treating the DCPD with selected clays.

Accordingly the invention provides a process for selectively reducing the 5-isopropenyl-2-norbornene content of a DCPD composition by contacting a 5-isopropenyl-2-norbornene containing DCPD composition with an acid clay.

Although it is known from Japanese Published Patent Application JP 02 17130 to treat DCPD with a catalyst selected from the group consisting of activated clay, acid clay, faujasite, X-type zeolite, Y-type zeolite, offretite/erionite, mordenite, ferrierite, silica alumina and strongly acidic ion-exchange resins, in order to isomerize endo-DCPD to the corresponding exo-isomer, and to thereby obtain a DCPD having a lower freezing point, no information is provided therein regarding the problem of how to increase the purity of DCPD, let alone which of the catalysts mentioned would be effective in such an operation. This aspect was apparently irrelevant in view of the availability of very pure DCPD, as in all the examples 99.8% pure DCPD was employed.

In the context of the present invention the term acid clay refers to a clay having Brønsted- or Lewis type acidity. Such clays are known and can be prepared by known technology from natural and synthetic clay minerals. Preferred clays whereon the acid clay for use in the process of the present invention may be based are smectite clays, such as exemplified by montmorillonite, saponite, hectorite, beidellite, nontronite and sauconite.

The hereinbefore mentioned known technology for the preparation of the acid clays includes methods such as for example submitting the corresponding natural or synthetic clay precursor to a cation-exchange procedure, or by treating the precursor clay with a mineral acid.

In the process of the present invention an acid montmorillonite clay is a preferred acid clay.

The acid clay/DCPD ratio in the process of the present invention will, to a large extent, be determined by not only the codimer content of the crude DCPD to be treated and the codimer requirements of the ultimate DCPD, but also by the acidity of the clay and the manner wherein and the conditions whereunder the process is to be conducted.

Although the codimer content of the crude DCPD to be purified in the process of the present invention is not critical, it is generally preferred to employ a crude DCPD having a codimer content $\leq 10\%$. To reduce the codimer content of a crude DCPD having a considerably higher codimer content, it is considered more advantageous to reduce the codimer content thereof by submitting the crude DCPD to a thermal-decomposition/recombination procedure, as described hereinbefore.

The requirements regarding the codimer content of the ultimate DCPD, will be largely governed by the nature of the polymerization catalyst as well as by the ultimate product requirements.

It will be appreciated that the acidity of the acid clay will be governed by a number of parameters, such as for example the nature of the cations which have been exchanged, the water content of the clay (a dried clay generally demonstrating a higher activity), the nature of the clay, the nature of the reaction medium, the pretreatment of the clay and temperature at which the process is to be conducted. In general submitting the acid clay to a heat treatment at a temperature in the range of from 80° to 100° C. at reduced pressure e.g. 0.1 bar (10 kPa), for at least 16 hours has proven to be sufficient.

As mentioned hereinbefore, also the manner wherein and conditions whereunder the DCPD is contacted with the acid clay may affect the DCPD/clay ratio. The present process may be conducted batchwise, i.e. under stationary conditions or under shear, or continuously.

The form wherein the acid clay may be employed in the process of the present invention is not critical, and includes clay in powder form, in the form of discrete particles, shaped, such as for example as an extrudate possessing a sufficient contact area, or as a supported clay, i.e. wherein the clay is present e.g. as a coating on an inert support or carrier. When employing the acid clay in powder form, such as for example in a batch process, best use is made of the large surface acid of the clay; on the other hand with this mode of operation, separating the DCPD from the dispersed clay may be more cumbersome than when using e.g. a clay extrudate. In a batch process good results have been obtained both in stationary conditions as well as under shear, employing a DCPD/acid clay ratio in the range of from 10:1 to 3:1.

When a continuous mode of operation is employed for conducting the process of the present invention, the DCPD may be passed through one or more colums packed with the acid clay. It is of course also possible to include the acid clay containing column as an element of a series of packed columns employed for other upgrading steps for improving the quality of DCPD.

The process of the present invention may in principle be conducted at any temperature between the freezing point of DCPD and its decomposition temperature. Conveniently the present process may be conducted at a temperature in the range of from 35° to 120° C. and preferably in a range of from 50° to 100° C.

Subsequent to the treatment with acid clay, any volatile compounds formed during said clay treatment may be flashed off.

The invention will be further illustrated by the following examples without restricting the scope of the invention, and for which the following information is provided:

| Ref | Compounds investigated for reducing the codimer content of DCPD: Acid clays | Typical acidity (mmol $H^+$/g) (conductometric) |
|---|---|---|
| A | Montmorillonite K-10 (ex Fluka) | 0.4 |
| B | $AlCl_3$ -treated montmorillonite* | 0.8 |
| C | HCl-treated montmorillonite* | 0.7 |
|   | "Reference compounds" | |
| a | Mol sieves 4 A (Linde A) | |
| b | Mol sieves 13 X (Linde X/faujasite) | |
| c | Zeolite ($NH_4^+$)Y (Linde Y/faujasite) | |
| d | Zeolite ($H^+$)Y (Linde Y/faujasite) | |
| e | ($H^+$)ZSM-5 (Intercat) | 0.8 |
| f | Na-montmorillonite* | neutral |
| g | Ion exchange resin Na/ion $H^+$ | 0.7 |

*These samples were laboratory prepared using known technology.

| Composition of crude DCPD used: Batch | I | II | III |
|---|---|---|---|
| DCPD (% m/m) | 93 | 93 | 93 |
| exo-DCPD (% m/m) | 0.6 | 0.8 | 0.7 |
| 5-isopropenyl-2-norbornene (% m/m) | 3.0 | 3.1 | 2.5 |
| 5-(propene-1-yl)-2-norbornene (% m/m) | 0.2 | 0.5 | 0.2 |
| tri-CPD (% m/m) | 0.2 | 0.6 | 0.6 |
| 5-methyltetrahydroindene (% m/m) | 0.6 | 1.0 | 1.0 |

ANALYSIS

The DCPD was analyzed before and after reaction, via gas liquid chromatography (GLD) employing a HP 5880 gas chromatograph equipped with a 50 m×0.2 mm×0.5 μm X-linked methyl-silicone (PONA Capillary Column), having an injection port temp.: 140° C., an oven temperature programme: 40° C.-200° C., and a programming rate: 4° C./min. Percentage (%) is expressed as m/m (mass on mass).

| Used abbreviations | |
|---|---|
| Isoprop. norb.: | 5-isopropenyl-2-norbornene |
| Trimer: | tri-CPD |
| THI: | 5-methyltetrahydroindene |

EXAMPLES I-III

DCPD and acid clay of the types and in the ratios as indicated in Table I were introduced into glass bottles and homogenized and subsequently placed on a roller table at 23° C. for 2 days. The resulting GLC-analysis data of the thus treated batches of DCPD are given in Table I.

COMPARATIVE EXPERIMENTS 1-7

The procedure of Examples I-III was repeated with the exception that the acid clays (Ref. A-C) were replaced with the reference compounds a-g. The resulting analytical data have been collected in Table II.

TABLE I

| Example | I | II | III |
|---|---|---|---|
| DCPD batch no. | I | II | II |
| Acid clay type | A | B | C |
| g Clay/10 ml DCPD | 1.67 | 1.11 | 1.11 |
| Isoprop. norb. (%) | 0.5 | 0.6 | 0.5 |
| Trimer (%) | 0.2 | 0.5 | 0.5 |
| Exo-DCPD (%) | 0.7 | 0.8 | 1.0 |
| THI (%) | 0.5 | 1.0 | 0.9 |

TABLE II

| Comp. exp. | 1 | 2 | 3 | 4 | 5 | 6 | 7 |
|---|---|---|---|---|---|---|---|
| DCPD batch no. | I | I | I | I | I | I | II |
| Compound type | a | b | c | d | e | f | g |
| g Compound/10 ml DCPD | 3.33 | 3.33 | 1.67 | 1.67 | 1.67 | 1.67 | 2.22 |
| Isoprop. norb. (%) | 2.9 | 1.7 | 3.0 | 2.8 | 3.0 | 3.0 | 2.9 |
| Trimer (%) | 0.2 | 0.2 | 0.2 | 0.2 | 0.2 | 0.2 | 0.5 |
| Exo-DCPD (%) | 0.6 | 1.5 | 0.7 | 0.7 | 0.6 | 0.6 | 0.5 |
| THI (%) | 0.6 | 0.4 | 0.6 | 0.5 | 0.6 | 0.6 | 1.0 |

EXAMPLE IV

The procedure of Example I-III was repeated with the exception that only the K-10 type clay was employed and in a ratio of 1 g/10 ml DCPD. In addition to being contacted at 23° C. duplicate samples were also placed on a roller table at 80° C. Before being analyzed the 80° C. samples were cooled down to ambient temperature. The corresponding analytical data have been collected in Table III.

COMPARATIVE EXPERIMENT 8

The procedure of Example IV was repeated with the exception that the K-10 clay was replaced with a 13 X mol sieve type compound (b), which was furthermore employed in a ratio of 2 g/10 ml DCPD. The analytical data have been collected in Table IV.

The data provided by Examples I-IV and by the comparative experiments 1-8 clearly demonstrate that the acid clays as described hereinbefore, are not only very effective in selectively reducing the 5-isopropenyl-2-norbornene content of crude DCPD, but are surprisingly considerably more effective in this respect than the zeolite-type compounds, the acid ion-exchange resin and the neutral clay which were included as reference.

TABLE III

| Example | IV | | | | | |
|---|---|---|---|---|---|---|
| DCPD Batch no. | III | | | | | |
| Clay type | A | | | | | |
| g/10 ml DCPD | 1 | 1 | 1 | 0 | 1 | 1 | 1 |
| Temperature °C. | 23 | | | 80 | | |
| Time h. | 0 | 1 | 5 | 0 | 0.1 | 1 | 5 |
| Isoprop. norb. (%) | 2.5 | 2.1 | 1.8 | 2.5 | 1.9 | <0.1 | <0.1 |
| Exo-DCPD (%) | 0.7 | 1.0 | 1.0 | 0.7 | 0.8 | 1.5 | 2.7 |

TABLE IV

| Comp. exp. | 8 | | | |
|---|---|---|---|---|
| DCPD Batch no. | III | | | |
| Compound type | b | | | |
| g/10 ml DCPD | 2 | | | |
| Temperature °C. | 23 | | 80 | |
| Time h. | 1 | 5 | 1 | 5 |
| Isoprop. norb. (%) | 2.4 | 2.2 | 1.9 | 1.2 |
| Exo-DCPD (%) | 1.0 | 1.0 | 3.0 | 5.4 |

We claim:

1. A process for selectively reducing the 5-isopropenyl-2-norbornene content of a dicyclopentadiene (DCPD) composition by contacting a 5-isopropenyl-2-norbornene containing DCPD composition with an acid clay.

2. A process as claimed in claim 1, wherein the acid clay is based on a smectite clay.

3. A process as claimed in claim 2, wherein the acid clay is selected from montmorillonite, saponate, hectorite, beidellite, nontronite and sauconite.

4. A process as claimed in claim 1, wherein the 5-isopropenyl-2-norbornene content of the DCPD composition is less than or equal to 10% by weight based on the total weight of the DCPD composition.

5. A process as claimed in claim 1, wherein the DCPD and acid clay are contacted at a temperature in the range of from 35° to 120° C.

6. A process as claimed in claim 1, wherein the DCPD and acid clay are contacted at a temperature in the range of from 50° to 100° C.

* * * * *